US 6,214,054 B1

(12) United States Patent
Cunanan et al.

(10) Patent No.: US 6,214,054 B1
(45) Date of Patent: Apr. 10, 2001

(54) METHOD FOR FIXATION OF BIOLOGICAL TISSUES HAVING MITIGATED PROPENSITY FOR POST-IMPLANTATION CALCIFICATION AND THROMBOSIS AND BIOPROSTHETIC DEVICES PREPARED THEREBY

(75) Inventors: Crystal M. Cunanan, Mission Viejo; Lillian Quintero, Garden Grove; Michael N. Helmus, Long Beach; Christine Loshbaugh, Irvine; H. Chris Sarner, Laguna Hills, all of CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/157,546

(22) Filed: Sep. 21, 1998

(51) Int. Cl.⁷ .................. A61F 2/24; A61L 27/00
(52) U.S. Cl. ............ 623/23.72; 623/901; 600/36; 606/265; 606/266
(58) Field of Search ............... 623/1, 2, 11, 16, 623/12, 66, 23.72, 901, 915, 917; 606/265, 266; 600/36

(56) References Cited

U.S. PATENT DOCUMENTS

| 4,120,649 | 10/1978 | Schecter . | |
|---|---|---|---|
| 4,648,881 | 3/1987 | Carpentier et al. . | |
| 4,729,139 | 3/1988 | Nashef . | |
| 4,885,005 | 12/1989 | Nashef et al. . | |
| 4,976,733 | 12/1990 | Girardot . | |
| 5,002,566 | 3/1991 | Carpentier . | |
| 5,437,287 | * | 8/1995 | Phillips et al. ............. 623/1 |
| 5,674,298 | * | 10/1997 | Levy et al. ............... 623/2 |

FOREIGN PATENT DOCUMENTS

| 103946 | 3/1984 | (EP) . |
|---|---|---|
| WO84/01879 | 5/1984 | (WO) . |
| WO 96/04028 | 2/1996 | (WO) . |
| WO 98/46288 | 10/1998 | (WO) . |

OTHER PUBLICATIONS

Carpentier et al; Continuing Improvements in Valvular Bioprostheses, J. Thorac Cardiovascular Surg., 83:27–42, 1982.

* cited by examiner

Primary Examiner—David J. Isabella
Assistant Examiner—Choon P. Koh
(74) Attorney, Agent, or Firm—Robert D. Buyan; Guy L. Cumberbatch

(57) ABSTRACT

A method for fixation of biological tissues, and bioprosthetic devices prepared by such method. The method generally comprises the steps of A) fixing the tissue, B) treating the tissue with a mixture of i) a denaturant, ii) a surfactant and iii) a crosslinking agent, C) fabricating or forming the bioprosthesis (e.g., forming the tissue and attaching any non-biological components thereto) and D) subjecting the bioprosthesis to terminal sterilization.

56 Claims, 5 Drawing Sheets

METHOD FOR FIXATION OF BIOLOGICAL TISSUES HAVING MITIGATED PROPENSITY FOR POST-IMPLANTATION CALCIFICATION AND THROMBOSIS AND BIOPROSTHETIC DEVICES PREPARED THEREBY

FIELD OF THE INVENTION

The invention pertains generally to medical method/devices and more particularly to a method for fixing (e.g., tanning or crosslinking) and sterilizing biological tissue to i) decrease the fixed tissue's propensity for post-implantation calcification and ii) decrease the thrombogenicity of the fixed tissue.

BACKGROUND OF THE INVENTION

Various types of implantable medical devices may be formed wholly or partially of biological tissue that has been chemically "fixed" or preserved. The technique used for chemical fixation of biological tissues typically requires exposure of the biological tissue to one or more chemical agents that are capable of forming cross-linkages between connective tissue protein molecules present in the tissue.

Examples of fixed biological tissues that have been used to form implantable bioprostheses include cardiac valves, blood vessels, skin, dura mater, pericardium, ligaments and tendons. These biological tissues typically contain connective tissue proteins (i.e., collagen and elastin) which act as the supportive framework of the tissue. The pliability or rigidity of each biological tissue is largely determined by the relative amounts of collagen and elastin present within the tissue and/or by the physical structure and confirmation of its connective tissue frame work.

Each Collagen molecule is made up of three (3) polypeptide chains intertwined in a coiled helical confirmation. The Chemical fixatives (i.e., tanning agents) which are used to preserve biological tissues generally form chemical cross-linkages between the polypeptide chains within a given collagen molecule (i.e., intramolecular crosslinkages), or between adjacent collagen molecules (i.e., intermolecular crosslinkages).

Examples of chemical fixative agents which have been utilized to cross-link collagenous biological tissues include; aldehydes (e.g., formaldehyde, glutaraldehyde, dialdehyde starch, para formaldehyde, glyceroaldehyde, glyoxal acetaldehyde, acrolein), diisocyanates (e.g., hexamethylene diisocyanate), carbodiimides, photooxidabon, and certain polyepoxy compounds (e.g., Denacol-810, –512, or related compounds). Of the various chemical fixatives available, glutaraldehyde is the most widely used. Glutaraldehyde is used as the fixative for many commercially available bioprosthetic products, such as porcine bioprosthetic heart valves (i.e., the Carpentier-Edwards® stented porcine bioprosthesis; Baxter Healthcare Corporation; Edwards CVS Division, Irvine, Calif. 92714-5686), bovine pericardial heart valve prostheses (e.g., Carpentier-Edwards® Pericardial Bioprosthesis, Baxter Healthcare Corporation, Edwards CVS Division; Irvine, Calif. 92714-5686) and stentless porcine aortic prostheses (e.g., Edwards® PRIMA Stentless Aortic Bioprosthesis, Baxter Edwards AG, Spierstrasse 5, GH6048, Horn, Switzerland).

One problem which has been associated with the implantation of bioprosthetic materials is that the connective tissue proteins (i.e., collagen and elastin) within these materials can become calcified following implantation within the body. Such calcification can result in undesirable stiffening or degradation of the bioprosthesis. Two (2) types of calcification-intrinsic and extrinsic--are known to occur in fixed collagenous bioprostheses, although the exact mechanism(s) by which such calcification occurs is unknown. Intrinsic calcification is characterized by the precipitation of calcium and phosphate ions within the fixed bioprosthetic tissue, including the collagen matrix and remnant cells. Extrinsic calcification is characterized by the precipitation of calcium and phosphate ions within the thrombus, including adherent cells (e.g., platelets) to the bioprosthesis and the development of calcium phosphate-containing surface plaques on the bioprosthesis.

The factors that affect the rate at which fixed tissue bioprostheses undergo calcification have not been fully elucidated. However, factors that are thought to influence the rate of calcification include:

a) patient's age;
b) existing metabolic disorders (i.e.,
c) hypercalcemia, diabetes, etc.);
d) dietary factors;
e) infection;
f) parenteral calcium administration;
g) dehydration;
h) distortion/mechanical factors;
i) inadequate coagulation therapy during initial period following surgical implantation; and
j) host tissue responses.

The factors that are thought to affect the propensity for platelets to adhere to a fixed bioprosthetic tissue include:

a) tissue damage;
b) diet;
c) surface properties of the tissue, including the nature of exposed collagen (e.g., type I, IV, etc.);
d) metabolic changes;
e) coagulation;
f) hemodynamics
g) inflammation; and,
h) infection.

Various techniques have heretofore been proposed for mitigating the in situ calcification of glutaraldehyde-fixed bioprostheses. Included among these calcification mitigating techniques are the methods described in U.S. Pat. No. 4,885,005 (Nashef et al.) entitled Surfactant Treatment of Implantable Biological Tissue To Inhibit Calcification; U.S. Pat. No. 4,648,881 (Carpentier et al.) entitled Implantable Biological Tissue and Process For Preparation Thereof; U.S. Pat. No. 4,976,733 (Girardot) entitled Prevention of Prosthesis Calcification; U.S. Pat. No. 4,120,649 (Schechter) entitled Transplants; U.S. Pat. No. 5,002,2566 (Carpentier) entitled Calcification Mitigation of Bioprosthetic Implants; EP 103947A2 (Pollock et al.) entitled Method For Inhibiting Mineralization of Natural Tissue During Implantation and WO84/01879 (Nashef et al.) entitled Surfactant Treatment of Implantable Biological Tissue to Inhibit Calcification; and, in Yi, D., Liu, W., Yang, J., Wang, B., Dong, G., and Tan, H.; *Study of Calcification Mechanism and Anticalcification On Cardiac Bioprostheses* Pgs. 17–22, Proceedings of Chinese Tissue Valve Conference, Beijing, China, June 1995.

There presently remains a need in the art for the development of new calcification-mitigating methods for fixing (i.e., tanning and crosslinking) and sterilizing biological tissues to provide bioprosthetic devices which are a) less likely to become calcified and b) less thrombogenic, following implantation within a patient's body.

SUMMARY OF THE INVENTION

Broadly stated, the present invention provides a method for chemical fixation and sterilization of biological tissue, comprising the steps of:

1. HARVEST/PREPARATION OF TISSUE—harvesting and preparing a biological tissue.
2. FIXATION OF TISSUE—contacting the biological tissue with a fixative agent such as an aldehyde (e.g., formaldehyde or glutaraldehyde) for a fixation time period (e.g., when 0.625% glutaraldehyde is used as the fixative the time period will be 0.5 hours to 14 days) to effect crosslinking of the connective tissue proteins within the tissue.
3. DSC TREATMENT—before or after performance of the fixation step (Step B above) the biological tissue is placed in contact with (e.g., immersed in) a denaturant/surfactant/crosslinking agent (DSC) solution at a temperature between 4 and 50 degrees C for a period of time ranging from 90 minutes to 35 hours). This DSC treatment step is typically performed before transportation of the biological tissue into a clean room or aseptic environment, but may additionally or alternatively be performed at other times such as after assembly of the bioprosthesis as described in more detail herebelow.
4. ASSEMBLY/FABRICATION OF PROSTHESIS—trimming or configuring the biological tissue (if necessary) and attaching any required non-biological components (e.g., stents, frames, suture rings, other hardware elements) thereto. This assembly/fabrication step is typically performed in a clean room or aseptic environment;
5. TERMINAL STERILIZATION—subjecting the biological tissue to a sterilant (e.g., a liquid sterilant such as 0.2–2.0% by weight glutaraldehyde solution) for a sterilization time period. A 0.625% glutaraldehyde solution may be used in combination with heat (i.e. warming above room temperature but below a temperature which would cause damage to the tissue of the bioprosthesis), as the sterilant. Alternatively, a suitable sterilant solution may comprise an osmotically balanced aqueous solution alone or in combination with a non-contacting source of sterilization (e.g., radiation, electron beam, UV, or other similar expedient), or include an aqueous solution of glutaraldehyde in combination with the above-described DSC mixture or some components of such DSC mixture. In instances where a 0.625% glutaraldehyde solution is used as the sterilant, the sterilization time period may be 1–6 days at 37 degrees C or 1–2 days at 50 degrees C). This terminal sterilization step may be performed after packaging of the bioprosthesis in its final container, thereby eliminating the need for any subsequent handling of the bioprosthesis until the time of implantation.

Further in accordance with the invention, there are provided various types of bioprosthetic articles that are wholly or partially formed of tissue that has been prepared by the above-summarized fixation/sterilization method of the present invention. Examples of specific biological tissues which may be utilized to prepare bioprosthetic articles in accordance with this invention include, but are not necessarily limited to: heart valves; venous valves; blood vessels; ureter; tendon; dura mater; skin; pericardium; cartilage (e.g., meniscus); ligament; bone; intestine (e.g., intestinal wall); and periostium.

Further aspects and objects of the present invention will become apparent to those skilled in the relevant art, upon reading and understanding the detailed description of presently preferred embodiments set forth herebelow.

Additional embodiments and aspects of the invention may become apparent to those of skill in the art upon reading and understanding of the detailed description and specific examples set forth herebelow.

DETAILED DESCRIPTION OF PREFERRED EMBODIMENTS

Figure 1:
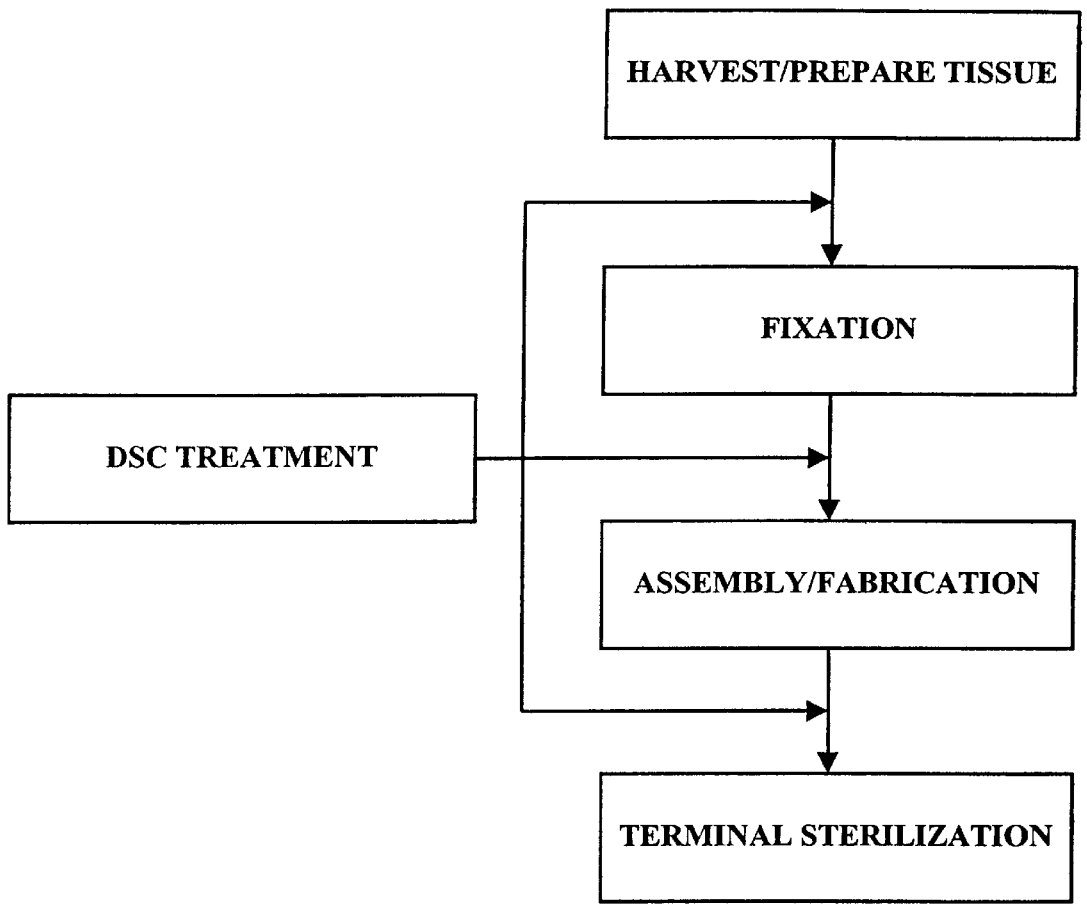
FIG. 1 is a general flow diagram of a calcification-mitigating treatment method of the present invention.

As shown in FIG. 1, the fixation/sterilization method of the present invention generally comprises six (6) steps as follows:

Step 1: Harvest/Prepare Biological Tissue

The desired biological tissue is harvested (i.e., surgically removed or cut away from its host animal). Thereafter, it is typically, trimmed or cut to size and washed with sterile water, balanced salt solution, saline or other suitable washing solution.

Step 2: Fixation of Biological Tissue

The biological tissue is then contacted with a crosslinking agent, such as an aldehyde (e.g., formaldehyde, glutaraldehyde, dialdehyde starch), polyglycidyl either (e.g., Denacol 810), diisocyanates, photooxidation, or carbodiimide(s)) to crosslink the connective tissue proteins present within the tissue. Due to the long standing use and experience with glutaraldehyde, a presently preferred fixative for use in this step is a solution of 0.2–2.0% by weight glutaraldehyde. For example, the biological tissue may be immersed in a solution of 0.625% by weight glutaraldehyde buffered to a pH of approximately 7.4 by a suitable buffer such as a phosphate buffer, for 0.5 hours to 14 days at 4–37 degrees C.

Step 3: Treatment With Denaturant/Surfactant/Crosslinking Agent (DSC Treatment)

a. Before or after fixation of the tissue in Step 2, the tissue is immersed in or otherwise contacted with a mixture containing i) a crosslinking agent, ii) a denaturing agent and iii) a surfactant (i.e., a DSC solution). One preferred DSC solution is a mixture of i) formaldehyde, ii) ethanol and ii) surfactant (e.g., Tween 80™ surfactant, available from ICI Americas, Brantford, Ontario). A preferred formulation for the DSC solution is as follows:

Formaldehyde . . . 0.1–10.0% (more pref. 4±0.4%) by weight

Ethanol . . . 1% to less than 60% (more pref. 2.2±2.2%) by weight

Tween 80 . . . 0.1–5.0% (more pref. 1.2 ±0.12%) by weight

The tissue is preferably immersed in the DSC solution for 2 to 24 hours and typically about 9 hours. During this immersion period, the DSC solution is maintained at a temperature of 4-50 degrees C, and typically about 20–37 degrees C.

Those skilled in the art will appreciate that various alternative chemical compounds or solutions may be substituted for each component of the DSC solution, as follows:

Potential Alternative Denaturing Agents
  A. Alcohols/Solvents: e.g., ethanol, isopropyl alcohol, acetone, ethers of small alkyl size (methyl, ethyl, propyl, isopropyl)
  B. Acidified Ethers: e.g., sulfuric acid/ether mixture
  C. Ketones: e.g., methyl ethyl ketone (MEK)
  D. Chlorofluorocarbon Solvents: e.g., Genesolve™ (Allied Signal, Inc., Morristown, N.J.)
  E. Glycols: glycerol ethylene glycol, polyethylene glycols of varying molecular weight
  F. Chaotropic Agents: e.g., urea, guanidine hydrochloride, guanidine thiocyanate potassium iodide
  G. High Concentration Salt Solutions: e.g., lithium chloride, sodium chloride, cesium chloride.

Potential Alternative Surfactants**

** these surfactant compounds can be used individually or in mixtures such as deoxycholate/Triton or commercially-available mixtures such as Micro-80/90.

A. Anionic Surfactants: e.g., esters of lauric acid, including but not limited to sodium laurel sulfate (also called sodium dodecyl sulfate)
  B. Alkyl sulfonic acid salts: e.g., 1-decanesulfonic acid sodium salt
  C. Non-ionic compounds: e.g., compounds based on the polyoxyethylene ether structures (including Triton X-100, 114, 405, N-101 available commercially from Sigma Chemical, St. Louis, Mo.), and related structures; Pluronic and Tetronic surfactants (available commercially from BASF Chemicals, Mount Olive, N.J.)
  D. Alkylated Phenoxypolyethoxy Alcohols: e.g., NP40, Nonidet P40, Igepal, CA630, hydrolyzed/functionalized animal and plant compounds including, Tween 80, Tween 20, octyl-derivatives, octyl b-glucoside, octyl b-thioglucopyranoside, deoxycholate and derivatives thereof, zwitterionic compounds, 3-([cholamidopropyl]-dimethyl ammonio)-1-propanesulfonate (CHAPS), 3-([cholamidopropyl]-dimethyl ammonio)-2-hydroxy-1-propanesulfonate (CHAPSO) available from Pierce Biotec Company, Rockford, Ill.

Potential Alternative Crosslinking Agents
  A. Aldehydes: formaldehyde, glutaraldehyde, paraformaldehyde, glyceraldehyde, glyoxal acetaldehyde or acrolein, dialdehyde starch
  B. Epoxies: e.g., any of the various Denacols and their individual reactive species, including mono, di, tri, and multi-functionalized epoxides
  C. Carbodiimides
  D. Diisocyanates
  E. Photooxidation Step 4: Assembly/Fabrication of Prosthesis After completion of Steps 1–3, and irrespective of the order in which Steps 2 and 3 were performed, the tissue is rinsed with a suitable rinsing solution such as isotonic saline or 0.625% glutaraldehyde. Thereafter, the tissue may be transported into a clean room or aseptic environment, and may be further trimmed or shaped (if necessary) and attached to or assembled with any non-biological components (e.g., stents, frames, suture rings, conduits, segments of polyester mesh to prevent suture tear-through, etc . . . ) To form the desired implantable bioprosthetic device. Examples of such assembled bioprosthetic devices include porcine bioprosthetic heart valves (i.e., the Carpentier-Edwards® stented porcine bioprosthesis; Baxter Healthcare Corporation; Edwards CVS Division, Irvine, Calif. 92714-5686), bovine pericardial heart valve prostheses (e.g., Carpentier-Edwards® Pericardial Bioprosthesis, Baxter Healthcare Corporation, Edwards CVS Division; Irvine, Calif. 92714-5686), stentless porcine aortic prostheses (e.g., Edwards® PRIMA Stentless Aortic Bioprosthesis, Baxter Edwards AG, Spierstrasse 5, GH6048, Horn, Switzerland), and biomechanical ventricular assist devices (e.g., the Novacor N-100PC model; Novacor, Oakland, Calif.).

Step 5: Treatment With Denaturant/Surfactant/Crosslinking Agent (DSC Treatment) (Optional)

Optionally, the DSC treatment described in Step 3 above may be carried out at this point in the procedure instead of as the third (3rd) step of the procedure. Or, if such DSC treatment has already been performed as the third (3rd) step of the procedure, it may be repeated at this point in the procedure (e.g., as the fifth (5th) step of the procedure).

Step 6: Terminal Sterilization

The bioprosthesis is immersed in or contacted with a terminal sterilant and heated for a period of time sufficient to ensure sterility of the bioprosthesis until the time of implantation. This terminal sterilization procedure is preferably carried out in the sealed container or package in which the bioprosthesis will be shipped and stored until the time of implantation.

A preferred terminal sterilant is 0.2–2.0% by weight glutaraldehyde, and most preferably about 0.25% by weight glutaraldehyde. Although DSC solution or compounds of the DSC solution can also be used. The preferred terminal sterilization time and temperature is 1–6 days at 37° C. or 1–2 days at 50° C.

Preparation of a Stented Pericardial Valve Bioprosthesis

The following is an example of the manner in which a stented pericardial bioprosthetic heart valve may be manufactured in accordance with the method of the present invention.

STEP 1: A bovine pericardial sac is obtained from a slaughterhouse, placed on ice, and transported to the location at which the bioprosthesis will be manufactured. Thereafter, the tissue is defatted and trimmed.

STEP 2: The tissue is washed with sterile isotonic saline solution and is thereafter immersed in a solution of 0.625% by weight glutaraldehyde buffered to a pH of approximately 7.4 by a suitable buffer such as a phosphate buffer, for approximately thirty minutes at room temperature. This results in crosslinking of the collagen present within the tissue.

STEP 3: The tissue is then removed from the fixative solution used in Step 2 and rinsed thoroughly with an aqueous solution of 0.625% (by weight) glutaraldehyde. Sometime thereafter, the DSC Treatment of Step 3 is carried out by immersing the tissue in DSC solution for 2 hours at ambient temperature. The DSC solution has the following formula:

Formaldehyde . . . 4.0±0.4% by weight
  Ethanol . . . 22±2.2% by weight
  Tween 80 . . . 1.2±0.12% by weight STEP 4: After completion of the DSC Treatment of Step 3, the tissue is removed from the DSC solution and leaflets are formed. Thereafter, the leaflets are mounted upon and sutured to a stent. Also, a needle-penetrable suture ring is attached about the inflow end of the valve to facilitate suturing of the bioprosthesis to the native tissue of the host patient. This completes the assembly and fabrication of the bioprosthetic heart valve.

STEP 5: Subject the finished valve after inspection to DSC treatment again for 9 hours at 37° C.

STEP 6: After the bioprosthesis is removed from the DSC solution it is transferred to a container which has been pre-filled with 0.25% glutaraldehyde aqueous solution buffered to a pH of 7.4 with sodium hydroxide such that the bioprosthetic valve is fully immersed in the buffered glutaraldehyde solution. Thereafter, the container is sealed and placed in an oven where it is heated to a terminal sterilization temperature of 37.5±2.5 degrees C for 25–27 hours. Thereafter, the container is cooled to room temperature and shipped to the hospital or other location(s) where it is stored until the time of implantation of the bioprosthetic valve.

Figure 2:
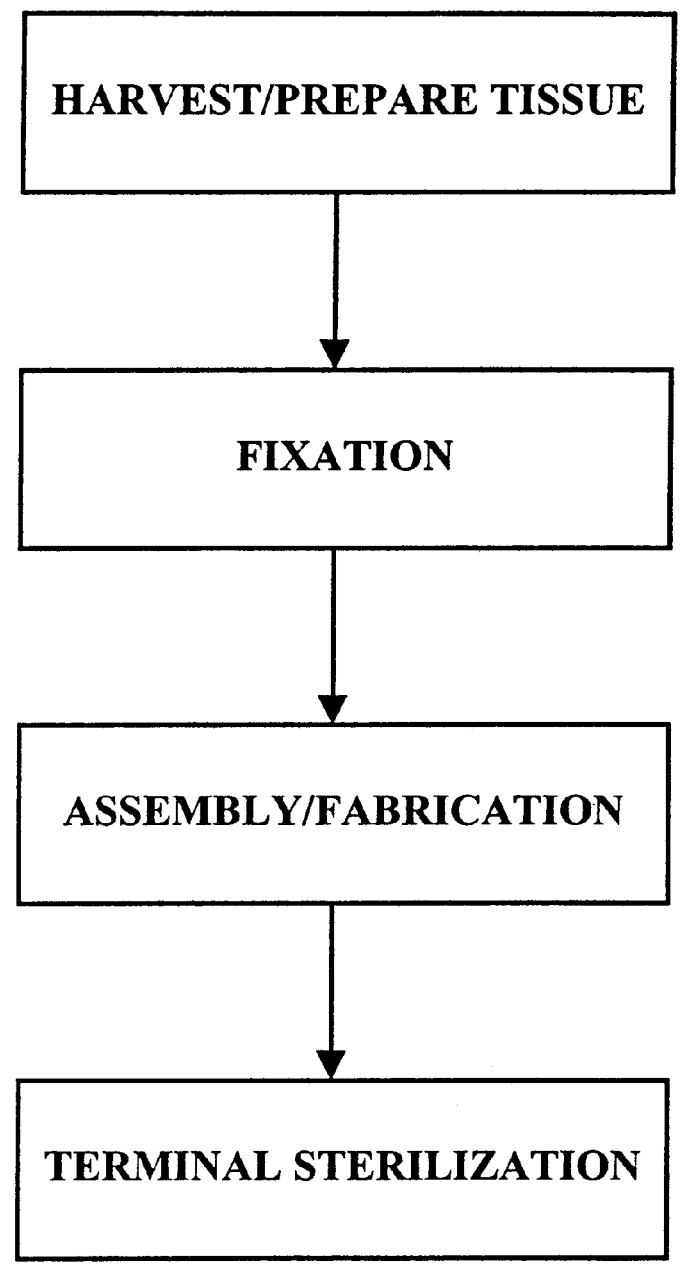
FIG. 2 is a general flow diagram of a treatment method used as a control in a study of the effectiveness of the present invention in mitigating calcification.
Figure 3:
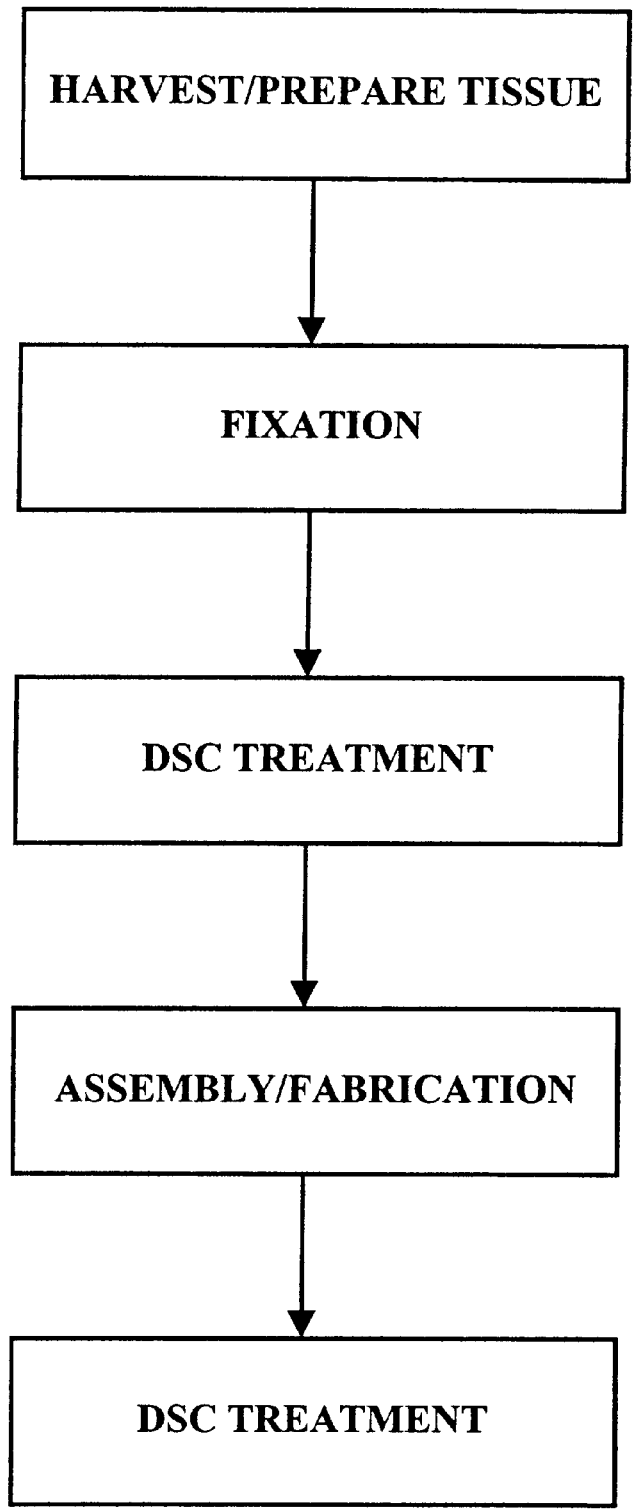
FIG. 3 is a general flow diagram of a treatment method used as a control in a study of the effectiveness of the present invention in improving hemocompatibility.

Studies were performed to objectively assess the benefits of the above-described process in mitigating calcification and improving hemocompatibility. First, the new process was compared with a process as shown in FIG. 2, which includes a terminal sterilization step after "assembly," but does not include any intermediate DSC steps. The assembly step in this case consisted of cutting pieces of fixed tissue into circles for subcutaneous implantation in animals. After a suitable period, the tissues were explanted and analyzed for calcium content, an indicator of calcification rate. In a second study, the new process was compared with a process as shown in FIG. 3, which includes intermediate DSC steps but does not include a terminal sterilization step. The resulting tissues were then exposed to whole blood for a period and the surfaces photographed using a scanning electron microscope to visibly determine any differences.

In the first comparison study, control tissues were generated by traditional glutaraldehyde fixation in conjunction with a terminal sterilization step as described above. In these tests, circular pieces of tissue prepared by the new method and by the control method were surgically placed in either the subcutaneous space in rats and rabbits, or in a pocket created in the paravertebral muscle in the rabbit. After thirty days implantation the tissues were excised from the host tissue, rinsed, and calcium content is determined by atomic absorption spectroscopy. The study results are as follows:

Determination of Calcium Content by Atomic Absorption Spectroscopy Tissues surgically implanted for Thirty days (ug Ca/mg tissue, dry weight)

| Implant site: | n: | Control: | n: | New process: |
|---|---|---|---|---|
| Rat subcutaneous | 6 | 124.04 ± 19.69 | 6 | 0.07 ± 0.18 |
| Rabbit subcutaneous | 6 | 95.35 ± 48.69 | 6 | 9.07 ± 7.88 |
| Rabbit intramuscular | 5 | 165.13 ± 22.88 | 4 | 86.15 ± 51.58 |

As is apparent, tissue produced according to the new process demonstrate reduced calcification in rat and rabbit implantation assays, and demonstrate the superiority of the new tissue preparation method compared to the control method.

The second study shows that tissues prepared according to the new method also demonstrate reduced adhesion of blood cells compared to a traditional treatment methods. The control method for the second study is seen in FIG. 3, and includes traditional glutaraldehyde fixation in conjunction with intermediate DSC steps. Scanning electron microscopy was used to assess the degree of adhesion of blood cells after exposure of anticoagulated whole human blood to tissues prepared according to the new method and to tissues prepared by the control method of FIG. 3. After a one hour exposure to whole human blood, the tissues were rinsed, critical point dried, lightly coated with gold and imaged in the SEI mode at an accelerating voltage of 5 kV in a JEOL 6300F field emission scanning electron microscope. The results are shown in FIGS. 4 and 5.

Figure 4:
FIG. 4 is a scanning electron microscope image of the surface of tissue treated in accordance with the method of FIG. 3.
Figure 5:
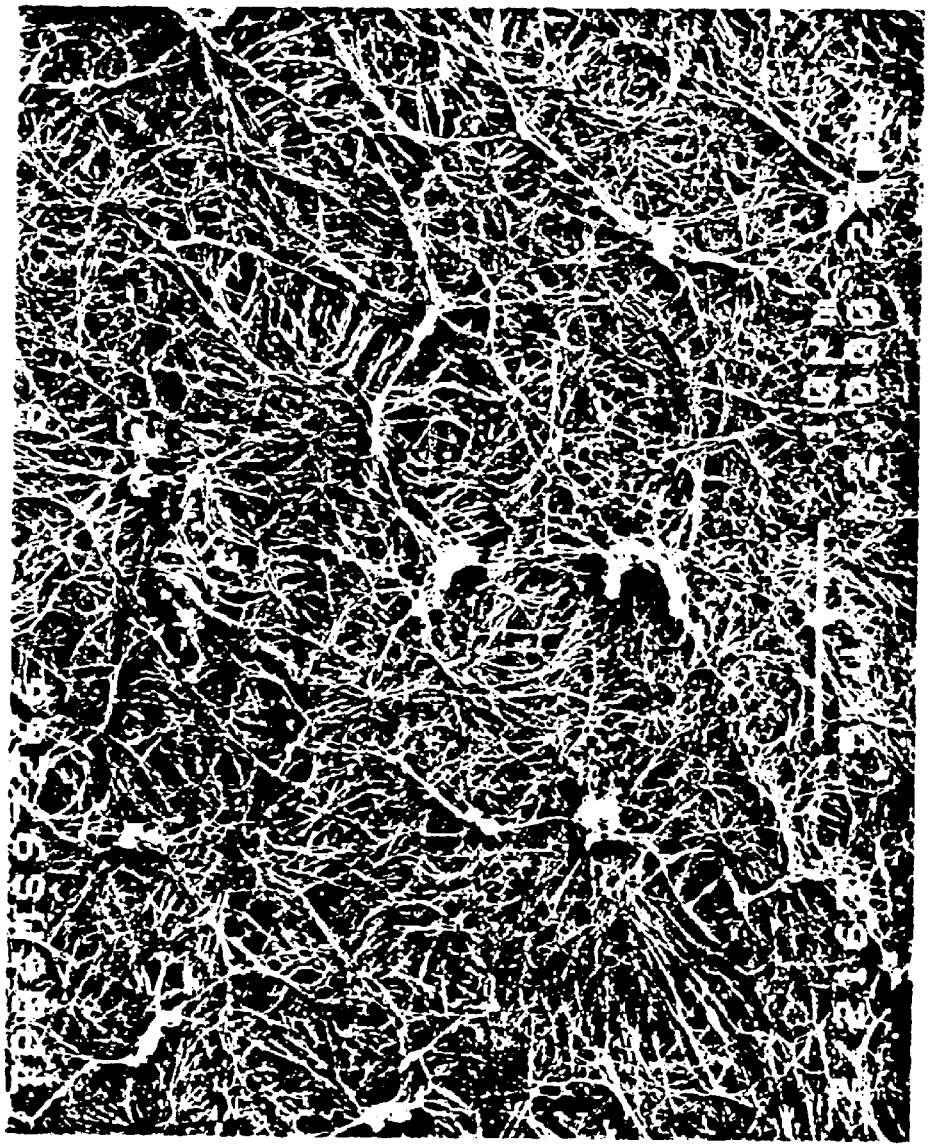
FIG. 5 is a scanning electron microscope image of the surface of tissue treated in accordance with the method of FIG. 1.

FIG. 4 shows an image from a representative area on the control tissues after exposure to whole human blood in vitro. Note numerous adherent cells and platelets on the surface. FIG. 5 shows an image from a representative area on tissues prepared by the new process after exposure to whole human blood in vitro. Note the nearly complete absence of adherent cells and platelets on the surface. These images demonstrate the improved hemocompatibility (i.e., reduced thrombogenicity) of the material prepared using the new process compared to the control method.

The invention has been described hereabove with reference to certain presently preferred embodiments or examples only, and no effort has been made to exhaustively describe all possible embodiments or examples of the invention. Those skilled in the art will recognize that various modifications, additions and changes may be made to the particular embodiments and examples described hereabove without departing from the intended spirit and scope of the invention. Accordingly, it is intended that all such modifications, additions and changes be included within the scope of the following claims.

What is claimed is:

1. A method for preparation of a bioprosthesis that contains connective tissue protein, said method comprising the steps of:
   a. contacting the connective tissue protein within the biological tissue with a fixative agent so as to cause crosslinking of connective tissue protein;
   b. contacting the biological tissue with a mixture of a denaturant, a surfactant and a crosslinking agent;
   c. assembling the bioprosthesis by performing any required shaping of the biological tissue and attaching any non-biological components of the prosthesis to the biological tissue; and,
   d. after completion of steps a. b and c. immersing the bioprosthesis in a liquid terminal sterilization solution and heating said terminal sterilization solution to a temperature between 35–50 degrees C.

2. The method of claim 1 wherein the fixative agent used in Step A comprises an aldehyde.

3. The method of claim 1 wherein the fixative agent used in Step A is selected from the group consisting of:
   a. diisocyanates,
   b. carbodiimides,
   c. photooxidation; and
   d. polyepoxy compounds.

4. The method of claim 1 wherein Step A comprises immersing the biological tissue in a solution containing 0.2–2.0% by weight glutaraldehyde for 0.5 hours-14 days at 4–37 degrees C.

5. The method of claim 1 wherein Step A is performed prior to Step B.

6. The method of claim 1 wherein Step B is performed before Step A.

7. The method of claim 1 wherein Step B is performed after Step C.

8. The method of claim 1 wherein Step B is performed before Step A and again before Step C.

9. The method of claim 1 wherein Step B is performed before Step A and again after Step C.

10. The method of claim 1 wherein Step B is performed after Step A and again after Step C.

11. The method of claim 1 wherein Step B is performed before Step A, again after Step A and again after Step C.

12. The method of claim 1 wherein the crosslinking agent of the mixture used in Step B is an aldehyde.

13. The method of claim 1 wherein the denaturing agent of the mixture used in Step B is an alcohol.

14. The method of claim 1 wherein the denaturing agent of the mixture used in Step B is selected from a group consisting of.
   a. acidified ethers;
   b. ketones;
   c. chlorofluorocarbon solvents;
   d. glycols;
   e. chaotropic agents; and
   f. high concentration salt solutions.

15. The method of claim 1 wherein the surfactant agent of the mixture used in Step B is selected from a group consisting of:
   a. anionic surfactants;
   b. alkyl sulfonic acid salts;
   c. non-ionic compounds; and
   d. alkylated phenoxypolyethoxy alcohols.

16. The method of claim 1 wherein the mixture used in Step B is a DSC solution which comprises:
   a. Formaldehyde . . . 0.1–10.0% by weight;
   b. Ethanol . . . 1% to less than 60% by weight; and,
   c. Tween 80 . . . 0.1–5.0% by weight.

17. The method of claim 16 wherein the mixture used in Step B is maintained at a temperature of at least 4 degrees C. but below 50 degrees C. while in contact with the biological tissue.

18. The method of claim 1 wherein the DSC solution used in Step B is maintained at a temperature of at least 4 degrees C. but below 50 degrees C. while in contact with the biological tissue.

19. The method of claim 1 wherein Step D further comprises:
   maintaining the temperature of said liquid terminal sterilization solution between 35–50 degrees C. for a period of time sufficient to ensure the sterility of the bioprosthesis until the time of implantation.

20. The method of claim 1 wherein the sterilant used in Step D is selected from the group of sterilants consisting of:
   a. liquid sterilants; and,
   b. a non-contacting sterilization source.

21. The method of claim 1 wherein Step D comprises immersing the bioprosthesis in a liquid terminal sterilization solution and heating said terminal sterilization solution to a temperature between 37–50 for a period of time sufficient to ensure the sterility of the bioprosthesis until the time of implantation.

22. The method of claim 21 wherein Step D is carried out in a sealed container and further comprises allowing the bioprosthesis to remain within said sealed container until the time of implantation.

23. The method of claim 21 wherein said terminal sterilization solution comprises an aqueous solution of 0.2–2.0% by weight glutaraldehyde buffered to a pH of approximately 7.4.

24. The method of claim 21 wherein said terminal sterilization solution comprises an osmotically balanced salt solution in the absence of other chemical sterilants and wherein the solution is heated to a temperature of at least 45 degrees C.

25. The method of claim 21 wherein the terminal sterilization solution comprises osmotically balanced salt solution in combination with at least one chemical sterilant.

26. The method of claim 21 wherein the terminal sterilization solution comprises at least one component selected from i) a denaturant, ii) a surfactant and iii) a crosslinking agent.

27. The method of claim 1 wherein Step D comprises:
   a. dispensing into a container a quantity of a terminal sterilant solution comprising 0.2–2.0% by weight glutaraldehyde buffered to a pH of approximately 7.4;
   b. immersing the bioprosthesis in said terminal sterilant solution within said container;
   c. sealing said container;
   d. heating said container, and the terminal sterilant solution and bioprosthesis contained therein, to a temperature of 37–50 degrees C. for 1–6 days;
   e. cooling said container, and the terminal sterilant solution and bioprosthesis contained therein, to room temperature; and,
   f. allowing said container to remain sealed until it is desired to implant the bioprosthesis in a mammalian patient.

28. A bioprosthesis comprising biological tissue having reduced potential for post-implantation calcification and thrombogenicity which has been fixed and sterilized by a method which comprises the steps of:
   a. crosslinking the connective tissue protein within the biological tissue with a fixative agent:
   b. contacting the biological tissue with a mixture of a denaturant, a surfactant and a crosslinking agent;
   c. assembling the bioprosthesis by performing any required shaping of the biological tissue and attaching any non-biological components of the prosthesis to the biological tissue; and,
   d. after completion of steps a, b and c, immersing the bioprosthesis in a liquid terminal sterilization solution and heating said terminal sterilization solution to a temperature between 35–50 degrees C.

29. The bioprosthesis of claim 28 wherein the fixative agent used in Step A comprises an aldehyde.

30. The method of claim 28 wherein the aldehyde fixative agent used in Step A is selected from the group consisting of:
   a. diisocyanates,
   b. carbodiimides,
   c. photooxidation; and
   d. polyepoxy compounds.

31. The bioprosthesis of claim 28 wherein Step A comprises immersing the biological tissue in a solution containing 0.2–2.0% by weight glutaraldehyde for 0.5 hours-14 days at 4–37 degrees C.

32. The bioprosthesis of claim 28 wherein Step A is performed prior to Step B.

33. The bioprosthesis of claim 28 wherein Step B is performed before Step A.

34. The bioprosthesis of claim 28 wherein Step B is performed after Step C.

35. The bioprosthesis of claim 28 wherein Step B is performed before Step A and before Step C.

36. The bioprosthesis of claim 28 wherein Step B is performed before Step A and again after Step C.

37. The bioprosthesis of claim 28 wherein Step B is performed after Step A and again after Step C.

38. The bioprosthesis of claim 28 wherein Step B is performed before Step A, again after Step A and again after Step C.

39. The bioprosthesis of claim 28 wherein the crosslinking agent of the mixture used in Step B is an aldehyde.

40. The bioprosthesis of claim 28 wherein the denaturing agent of the mixture used in Step B is an alcohol.

41. The bioprosthesis of claim 28 wherein the denaturing agent of the mixture used in Step B is selected from a group consisting of:
   a. acidified ethers;
   b. ketones;
   c. chlorofluorocarbon solvents;
   d. glycols;
   e. chaotropic agents; and
   f. high concentration salt solutions.

42. The bioprosthesis of claim 28 wherein the surfactant agent of the mixture used in Step B is selected from a group consisting of:
   a. anionic surfactants;
   b. alkyl sulfonic acid salts;
   c. non-ionic compounds; and
   d. alkylated phenoxypolyethoxy alcohols.

43. The bioprosthesis of claim 28 wherein the mixture used in Step B is a DSC solution which comprises:
   a. Formaldehyde . . . 0.1–10.0% by weight;
   b. Ethanol . . . 1% to less than 60% by weight; and,
   c. Tween 80 . . . 0.1–5.0% by weight.

44. The bioprosthesis of claim 43 wherein the mixture used in Step B is maintained at a temperature of at least 4 degrees C but below 50 degrees C while in contact with the biological tissue.

45. The bioprosthesis of claim 28 wherein the mixture used in Step B is maintained at a temperature of at least 4 degrees C. but below 50 degrees C while in contact with the biological tissue.

46. The bioprosthesis of claim 28 wherein Step B comprises:
   a. immersing the biological tissue in a solution containing 0.1–10.0% by weight formaldehyde, 1% to less than 60% by weight ethanol and 0.1–5.0% by weight of a surfactant; and,
   b. maintaining said solution at a temperature of at least 4 degrees C. but below 50 degrees C. for 1–36 hours.

47. The bioprosthesis of claim 28 wherein the sterilant used in Step D is selected from the group of sterilants consisting of:
   a. liquid sterilants; and,
   b. a non-contacting sterilization source.

48. The bioprosthesis of claim 28 wherein Step D of the method by which the bioprosthesis is fixed and sterilized further comprises:
   maintaining the temperature of said liquid terminal sterilization solution between 35–50 degrees C. for a period of time sufficient to ensure the sterility of the bioprosthesis until the time of implantation.

49. The bioprosthesis of claim 48 wherein Step D is carried out in a sealed container and further comprises allowing the bioprosthesis to remain within said sealed container until the time of implantation.

50. The bioprosthesis of claim 48 wherein said terminal sterilization solution comprises an aqueous solution of 0.2–2.0% by weight glutaraldehyde buffered to a pH of approximately 7.4.

51. The bioprosthesis of claim 48 wherein said terminal sterilization solution comprises an osmotically balanced salt solution in the absence of other chemical sterilants and wherein the solution is heated to a temperature of at least 45 degrees C.

52. The bioprosthesis of claim 48 wherein the terminal sterilization solution comprises osmotically balanced salt solution in combination with at least one chemical sterilant.

53. The bioprosthesis of claim 48 wherein the terminal sterilization solution comprises at least one component selected from i) a denaturant, ii) a surfactant and iii) a crosslinking agent.

54. The bioprosthesis of claim 28 wherein Step D comprises:
   a. dispensing into a container a quantity of a terminal sterilant solution comprising 0.2–2.0% by weight glutaraldehyde buffered to a pH of approximately 7.4;
   b. immersing the bioprosthesis in said terminal sterilant solution within said container;
   c. sealing said container;
   d. heating said container, and the terminal sterilant solution and bioprosthesis contained therein, to a temperature of 37–50 degrees C. for 1–6 days;
   e. cooling said container, and the terminal sterilant solution and bioprosthesis contained therein, to room temperature; and,
   f. allowing said container to remain sealed until it is desired to implant the bioprosthesis in a mammalian patient.

55. A method according to claim 1 wherein Step b is performed prior to Step c, and wherein Step b is then repeated between Steps c and d.

56. A bioprosthesis according to claim 1 wherein Step b of the method by which the bioprosthesis is fixed and sterilized is performed prior to Step c, and wherein Step b is then repeated between Steps c and d.

* * * * *

UNITED STATES PATENT AND TRADEMARK OFFICE
CERTIFICATE OF CORRECTION

PATENT NO.   : 6,214,054 B1
DATED        : April 10, 2001
INVENTOR(S)  : Crystal M. Cunanan, Lillian Quintero, Michael N. Helmus, Chirstine Loshbaugh, Christine Sarner It is certified that error appears in the above-identified patent and that said Letters Patent is hereby corrected as shown below:

CLAIMS:

Claim 3,
Line 5, after the word "photooxidation" insert -- agents --.

Signed and Sealed this

Twenty-eighth Day of August, 2001

Attest:

NICHOLAS P. GODICI
Attesting Officer   Acting Director of the United States Patent and Trademark Office

UNITED STATES PATENT AND TRADEMARK OFFICE
CERTIFICATE OF CORRECTION

PATENT NO. : 6,214,054 B1 Page 1 of 1
DATED : April 10, 2001
INVENTOR(S) : Crystal M. Cunanan et al.

It is certified that error appears in the above-identified patent and that said Letters Patent is hereby corrected as shown below:

<u>Title page,</u>
Item [75], Inventor(s), should read as follows:
-- Alain F. Carpentier, Paris, FR; Sophie Carpentier, Paris, FR; Crystal M. Cunanan, Mission Viejo; Lillian Quintero, Garden Grove; Michael N. Helmus, Long Beach; Christine Loshbaugh, Irvine; H. Chris Sarner, Laguna Hills, all of CA (US). --

Signed and Sealed this

Sixteenth Day of December, 2003

JAMES E. ROGAN
*Director of the United States Patent and Trademark Office*